United States Patent [19]

Hultgren

[11] Patent Number: 4,722,611

[45] Date of Patent: Feb. 2, 1988

[54] APPARATUS AND PROCESS FOR MONITORING THE COOLING PROPERTIES OF LIQUID QUENCHANTS AND RESTORING USED QUENCHANTS

[75] Inventor: David H. Hultgren, Buzzards Bay, Mass.

[73] Assignee: Union Carbide Corporation, Danbury, Conn.

[21] Appl. No.: 839,321

[22] Filed: Mar. 13, 1986

[51] Int. Cl.$^4$ .................. G01N 25/18; G01N 25/20; G01N 25/00
[52] U.S. Cl. ........................ 374/43; 374/45; 374/57
[58] Field of Search .............. 374/43, 44, 45, 54, 374/57; 73/53

[56] References Cited

U.S. PATENT DOCUMENTS

| | | | |
|---|---|---|---|
| 2,330,599 | 9/1943 | Kuehni | 73/51 |
| 2,587,622 | 3/1952 | Jaffe | 374/43 |
| 2,730,894 | 1/1956 | Husa | 374/43 |
| 2,876,327 | 3/1959 | Leisey | 219/20 |
| 2,937,334 | 5/1960 | Bolston et al. | 324/34 |
| 3,013,427 | 12/1961 | Bender | 374/43 |
| 3,161,782 | 12/1964 | Vieth | 307/88.5 |
| 3,236,099 | 2/1966 | Warthen | 73/204 |
| 3,333,470 | 8/1967 | Fingerson | 73/362 |
| 3,353,589 | 11/1967 | Tope | 165/26 |
| 3,457,770 | 7/1969 | Schroeer | 73/15 |
| 3,597,676 | 8/1971 | Moore | 323/20 |
| 3,683,671 | 8/1972 | Van Swaay | 73/27 |
| 3,695,095 | 10/1972 | Lineberg | 374/54 |
| 3,699,813 | 10/1972 | Lamb | 73/342 |
| 3,712,116 | 1/1973 | Andre | 73/53 |
| 3,968,677 | 7/1976 | Felton, Jr. et al. | 374/43 |
| 4,106,331 | 8/1978 | Bunton et al. | 374/43 |
| 4,143,549 | 3/1979 | Koehler | 73/342 |
| 4,255,962 | 3/1981 | Ashman | 374/44 |
| 4,344,315 | 8/1982 | Moxon et al. | 374/44 |
| 4,364,677 | 12/1982 | Ashman | 374/44 |
| 4,412,752 | 11/1983 | Cellitti et al. | 374/43 |
| 4,488,821 | 12/1984 | Wenckus | 374/44 |
| 4,563,097 | 1/1986 | Katafuchi | 374/43 |

FOREIGN PATENT DOCUMENTS 2574751 1/1978 U.S.S.R. .

Primary Examiner—Charles Frankfort
Assistant Examiner—Thomas B. Will
Attorney, Agent, or Firm—Steven H. Flynn

[57] ABSTRACT

An apparatus for testing the quench-cooling properties of a liquid quenchant includes a thermistor that is adapted to be immersed in the liquid to be tested. An electrical potential is applied across the thermistor, which is contained in one leg of an electrical bridge circuit. A first timer controls the duration of time during which the voltage is applied to the bridge circuit. A voltmeter is connected across the bridge circuit for indicating changes in the bridge balance due to changes in the resistance of the thermistor. The thermistor changes resistance in accordance with the thermal conductivity of the liquid in which it is immersed. Therefore, the quenchant properties of the liquid being tested are determinable by comparing the voltage output of the bridge when the thermistor is immersed in the test liquid with at least one reference voltage output obtained by immersing the thermistor in a reference liquid quenchant. Each test is conducted for the same amount of time, which is controlled by the timer. A process is provided for testing liquid quenchants, particularly used quenchants that can be restored to their original properties by the addition of polymer quenchant additives, or solvents such as water.

16 Claims, 7 Drawing Figures

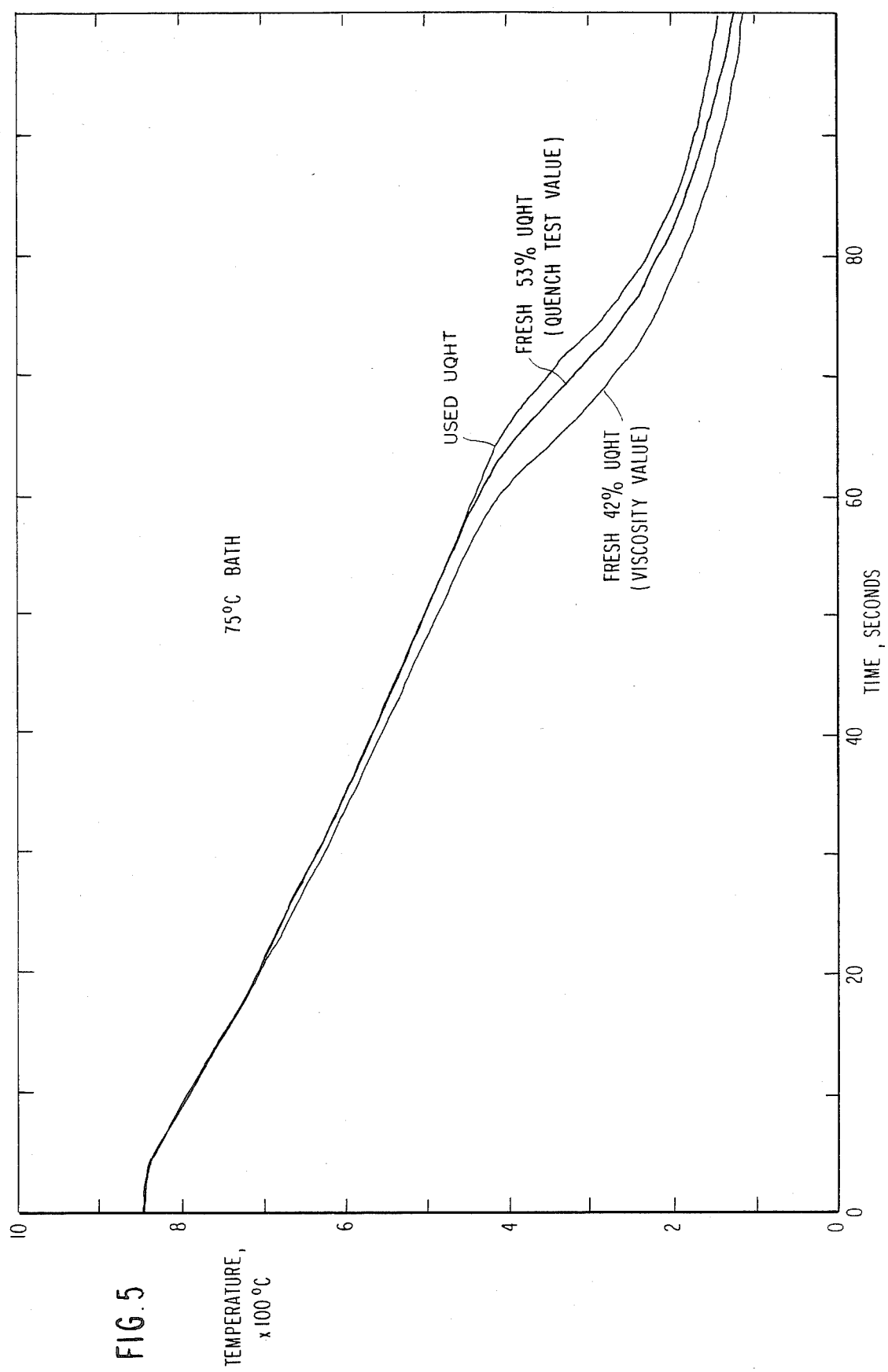

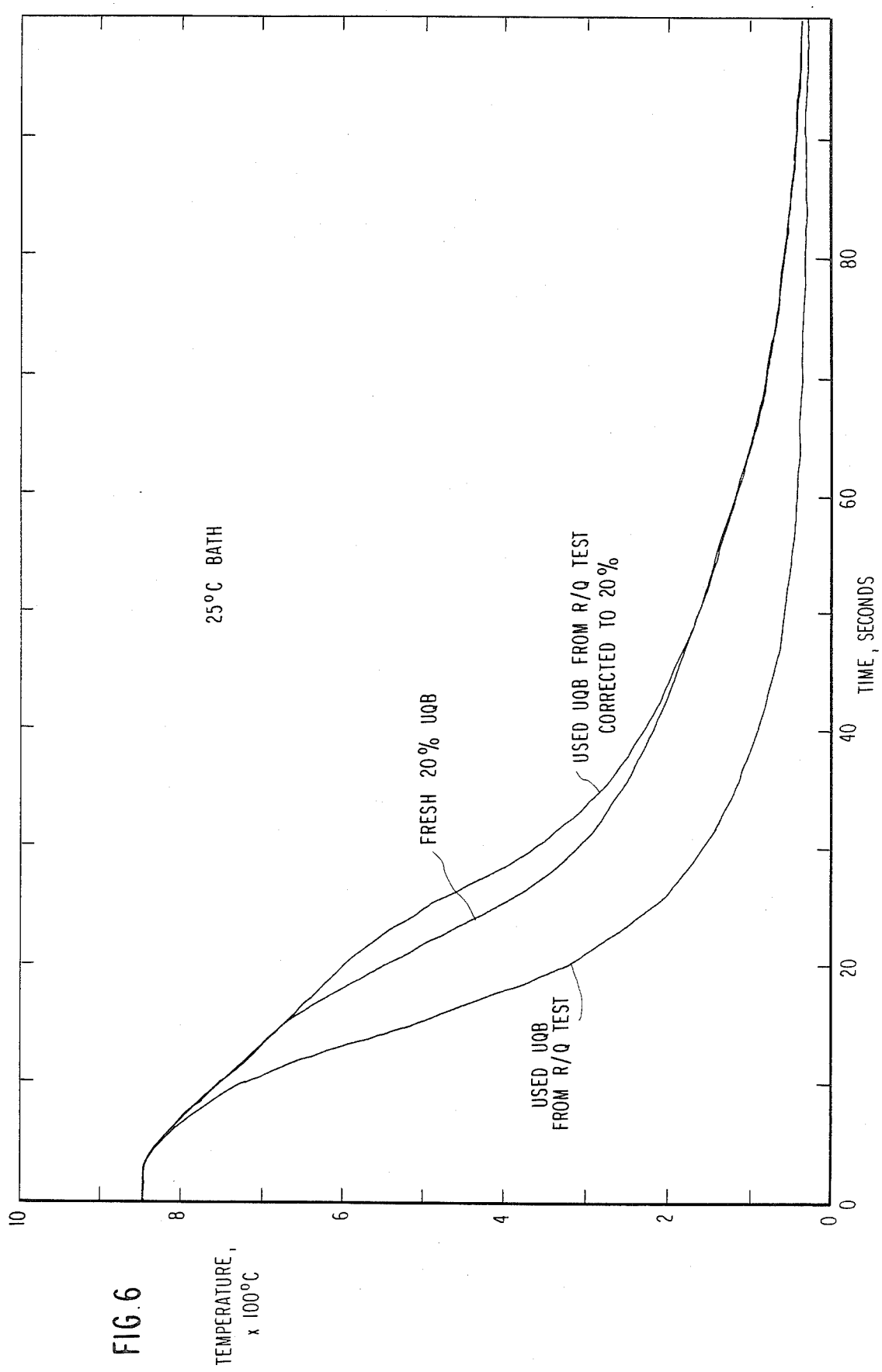

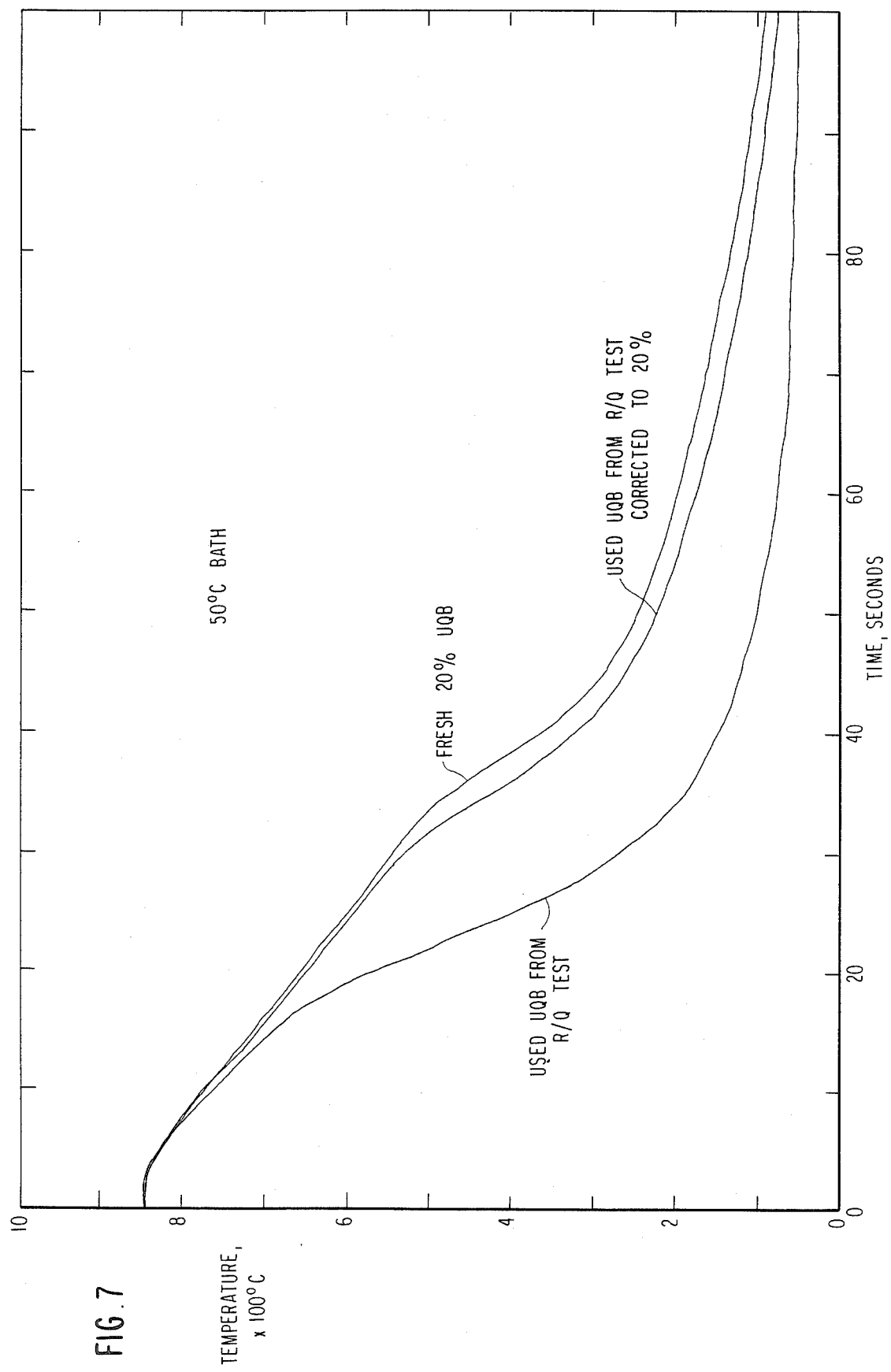

APPARATUS AND PROCESS FOR MONITORING THE COOLING PROPERTIES OF LIQUID QUENCHANTS AND RESTORING USED QUENCHANTS

BACKGROUND OF THE INVENTION

This invention relates to testing apparatus for measuring thermal properties of a liquid quenchant, particularly to apparatus and process steps for monitoring the cooling properties of polymer quenchants, and apparatus and process steps for monitoring the coolant properties of used liquid quenchants and altering their properties, e.g., restoring the cooling properties of the used liquid quenchants to their original, unused condition.

Thermally-responsive elements, known as thermistors, consist of semi-conductors having a negative temperature coefficient of resistance, i.e., have the characteristics of decreasing resistance with the increasing temperature. The thermistors are hard, ceramic-like, semi-conductors. They are available in at least three distinct forms; beads, discs or washers, and rods. All of these types are made of various mixtures of the oxides of magnesium, nickel, cobalt, copper, uranium, iron, zinc, titanium, and manganese. The mixtures of oxides are formed into the desired shapes and sintered under accurately controlled atmospheric and temperature conditions. They are characterized by being small and compact in size, are highly stable, are mechanically rugged and shock resistant, are provide with permanent electrical contacts, have a wide range of resistance to temperature coefficient and power dissipation, and have substantially unlimited life when operated within their maximum temperature rating. Typically, they are designed to have a specific negative coefficient of resistance, i.e., their resistance will change from several thousand ohms at 25° C. to near zero at 500° C.

Thermistors are known to be useful for detecting various properties of fluids. For example, thermistors are often positioned in gas and liquid streams to detect changes in thermal conductivity as it relates to flow rate or flow stoppage. For example, see U.S. Pat. No. 3,236,099, in which a bridge circuit including two thermistors is used in apparatus for indicating material stream flow characteristics by calorimetry. In most cases, the thermistor circuit is simple used to activate an alarm or control function.

Thermistors are often used as temperature sensing probes in resistance thermometers. For example, see U.S. Pat. Nos. 2,876,327; 3,699,813 and 4,143,549, which utilize thermistors in conjunction with Wheatstone bridge circuits. In this particular application, they are subjected to external heating, but in other applications they may be subjected to internal heating by the application of an appropriate electric potential. When voltage is applied to a thermistor and resistor in series a current will flow in the circuit. This electrical current causes heat to be generated in the thermistor, which in turn causes the resistance of the thermistor to be lessened and permits more current to flow than if the resistance had remained constant. This process continues until the thermistor reaches the maximum temperature possible for the amount of power available in the circuit, at which time a steady state will exist, i.e., the electrical energy applied is equal to the heat energy given off by the thermistor and resistor. Of course, the medium surrounding the thermistor will affect the equilibrium temperature.

U.S. Pat. No. 4,364,677 discloses apparatus comprising a bridge circuit which includes two thermoresistant devices such as thermistors which are used in heated probes for comparing the thermal conductivity of a gemstone to that of a standard stone such as a diamond. Other systems for thermal testing of solids are disclosed in U.S. Pat. Nos. 4,488,821 and 3,457,770. For example, the steady state temperature attained in air will be significantly higher than that for a liquid. Even minor differences in the thermal conductivity of liquids will have an effect.

The application of thermistors in devices used to measure the mixture ratio of a two-component gas mixture is known, (see, e.g., U.S. Pat. No. 3,683,671) but no such use with liquid mixtures has been found in the prior art. In particular, no reference to the use of thermistor circuits for determination of used liquid quenchant quality has been found in the prior art, nor is use of a thermistor known for testing used quenchants to determine the amount of quenchant additives to be added to the used quenchant to bring its quenching properties to the desired level.

U.S. Pat. No. 2,937,334 disclosed heat transfer testing apparatus for evaluating the heat transfer capacity of materials including quenching media, comprising a heated metal probe and electronic circuitry including a bridge circuit for determining the occurrence of the Curie point as the metal probe cools. The use of a thermistor is neither disclosed nor suggested. U.S. Pat. No. 3,333,470 discloses a method and apparatus for sensing fluid properties, including a resistance-type temperature sensor and a bridge circuit for maintaining at constant temperature. The system measures heat transfer between the sensor and its environment, which information can be used in the measurement of temperatures, velocities, concentrations and like properties of fluids. The use of a thermistor as the sensor is not suggested, and a method of determining a fluid's concentration is not indicated.

Heating and subsequent cooling is a process used to change the physical properties of various metals, such as steel and aluminum alloys. The overall cooling rate as well as the cooling rate at intermediate temperatures is critical in the quenching process, as these quantities, in combination with the composition of the metal, control to a great degree the final structural properties of the heat treated part. Many different liquids have been employed as quenchants over the years, including water, various oils, and even human blood.

Aqueous solutions of synthetic organis polymers have gained wide acceptance as quenching media in the last two decades. These products not only provide cooling characteristics intermediate between the fast quenching action of water and the relatively slow action of oil, but also provide a high degree of flexibility in that the desired cooling rate is set by adjustment of the polymer to water ratio. The most commonly used polymer quenchants are polyalkylene glycols, polyvinvylpyrrolidones and polyacrylates, with the polyalkylene glycol materials being by far the most common.

When a water quenchant loses its quenching properties due to contamination or an oil quenchant becomes contaminated or degraded, the quenchant is generally replace, purified or reconditioned. However, to insure the satisfactory operation of polymer-containing quenchants, the bath temperature, degree of agitation and optimum polymer concentration must be established and maintained. This is most often done by refractive index and kinematic viscosity measurement. The polymer concentration is most often determined by the end user through the use of a hand held refractometer. Kinematic viscosity measurement is used as an alternate method when the presence of bath contaminants such as inorganic salts affect the accuracy of the refractometer. However, after prolonged use or under unusually severe operating conditions, a significant increase in the water-soluble contaminants present and/or a molecular weight change in the polymer due to degradation may alter the bath to a point that the original viscosity-quenching action relationship is no longer valid.

These measuring techniques, moreover, relate only to fresh polymer solutions and are affected by the presence of soluble contaminants and the eventaul degradation of the polymer. When this condition occurs the quenching bath is typically checked by cooling curve analysis. This a a rather cumbersome laboratory procedure that entails the use of a temperature instrumented metal probes that are heated and immersed in baths of fresh and used quenchant solutions for the development of comparative cooling rate values.

It would be desirable to have available a portable cooling curve apparatus for use in the field, but this approach is not particularly practical from the standpoint of unit cost and operational complexity. However, a simple heat transfer (thermal conductivity) test designed to simulate fluid quenching action of a liquid quenchant would have merit.

SUMMARY OF THE INVENTION

Accordingly, it is an object of the present invention to provide a device for sensing the relative heat transfer characteristics of liquid quenching media, including water, organic liquids such as oils and in particular aqueous polymer solutions.

It is also an object of the present invention to provide a techinique wherein the heat transfer information developed with the test device of the present invention may be used to determine and alter the polymer/water relationship of an aqueous polymer quenchant solution and thereby achieve an altered cooling rate for the quenchant solution.

It is a further object of the present invention to measure the relative heat transfer characteristics of a liquid quenchant, and use the measurements obtained to restore a used quenchant solution to its original quenchant properties by addition of suitable amounts of additives, solvents or diluents based upon the measurements of the used quenchant.

It is a still further object of the present invention to provide portable apparatus and a method for quickly and conveniently testing the thermal properties of liquid quenchants, preferably providing greater sensitivity than tests of refractive index and/or viscosity.

In accordance with the present invention, apparatus is provided for testing the quench-cooling properties of a liquid quenchant, comprising:

a thermistor adapted to be immersed in the liquid to be tested;

means for applying an electrical potential across the thermistor, comprising means for applying an excitation voltage to a Wheatstone bridge circuit which contains the thermistor in one leg thereof;

first timing means controlling the duration of time during which said electrical potential is applied across said thermistor; and means for determining the electrical resistance of the thermistor, whereby the quenchant properties of the liquid tested are determined by comparison of the resistance of the immersed thermistor with at least one reference resistance value, e.g., the reference current value for water or a know quenchant solution.

The thermistor is positioned in direct thermal contact with the liquid to be tested. Electrical power to produce internal heating of the thermistor is provided by a variable voltage direct current power supply coupled to the bridge circuit. A voltmeter bridged between the two parallel branches of the bridge circuit indicates when the thermistor is at the prescribed temperature (as indicated by a bridge balance condition) or indicates the degree of deviation from that temperature.

The method of fluid evaluation with the quenchant tester may be described by the series of events which take place during three test operations. In the first operation, the supply voltage to the bridge circuit is adjusted to give a bridge balance condition with the thermistor immersed in water. Next, without changing the voltage setting the thermistor is positioned in a fresh quenchant solution having a known polymer concentration. The bridge circuit unbalance shown on the voltmeter is noted. In the third operation, again without changing the voltage setting, a used quenchant(s) of the same type as the fresh material is checked and the voltage unbalance reading on the voltmeter is noted. In the first operation, a baseline condition is established with water, i.e., no polymer present. In the second operation, a reference value is established for a fresh quenchant with a known polymer concentration for subsequent comparison with a used material in the third operation.

The device of this invention is a portable, relatively inexpensive and easy to use device that efficiently and accurately measures the cooling characteristics of used polymer quenchants, yet is not affected by contaminants or physical changes in the polymer solution.

Further in accordance with the invention, a process is provided for testing the quench-cooling properties of a liquid quenchant, comprising the steps of:

(a) using a thermistor to test a liquid quenchant sample, the thermistor being connected in a leg of a Wheatsonte bridge circuit and adapted to be immersed in the sample;

(b) determining the electrical resistance of the thermistor using means for measuring the output voltage of the bridge circuit, and (c) comparing the output voltage measured to at least one comparison measurment value, e.g., the measurement value of water or quenchant of known composition.

In a preferred embodiment, the apparatus and process of the present invention are used for testing used liquid quenchants comprising aqueous polymer solutions, so that the quenchants' thermal properties can be altered (e.g., restored to their original value) by the addition or additives or water.

Further details, objects and advantages of the present invention will be apparent from the following detailed description of a preferred embodiment shown schematically in the drawings, and the appended claims.

BRIEF DESCRIPTION OF THE DRAWINGS

FIG. 5 shows a set of quenchant cooling curves similar to those shown in FIG. 4 but having a different bath temperature;

FIG. 6 is set of quenchant cooling curves similar to FIG. 5, but hving a differing bath temperature; and FIG. 7 is a set of quenchant cooling curves similar to those shown in FIG. 6 but having a differing bath temperature and illustrating the utility of the present process to restore the thermal properties of used quenchant to nearly those of unused or fresh quenchant.

DETAILED DESCRIPTION OF THE DRAWINGS

Figure 1:
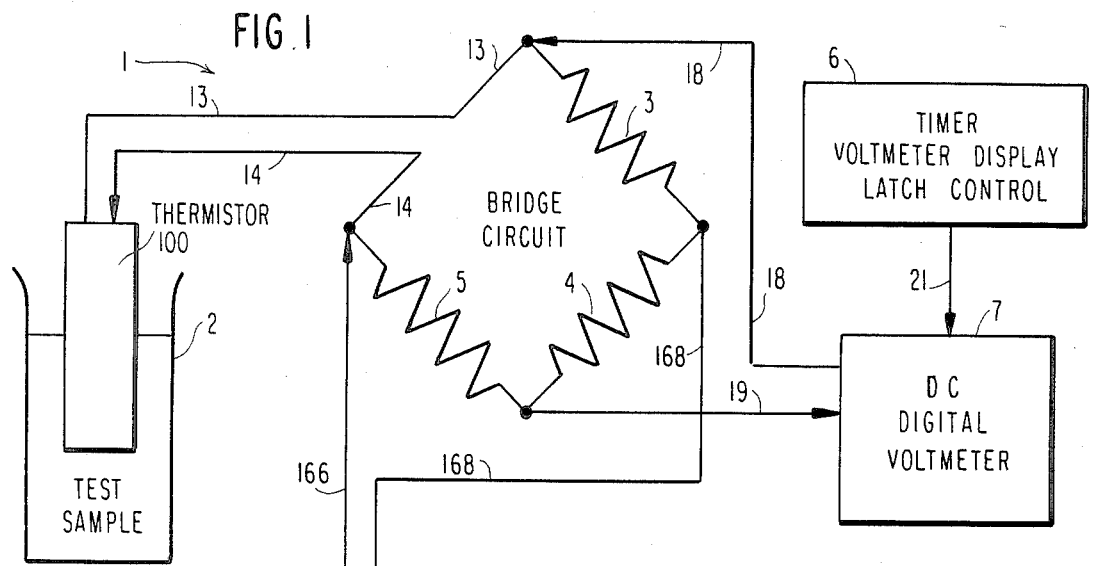
FIG. 1 is a schematic view of an electrical apparatus used in the present invention.

The quenchant tester apparatus and method of the present invention are based upon the principle that the equilibrium values of temperatures and current flow attained in a thermistor having an electrical potential imposed on it and immersed in a liquid are dependent upon the thermal conductivity of the liquid.

The steady state temperature of the apparatus of the present invention with the thermistor positioned in air is significantly higher than that for a liquid. Even minor differences in the thermal conductivity of liquids will have an effect. It is on this principle also that the quenchant tester of this invention is based.

The quenchant test device of this invention is based on a thermal conductivity measurement technique wherein a thermistor acts as a combined heat input and temperature measurement source for the establishment of heat flow rate to the quenchant, or conversely indicate the cooling rate of the quenchant.

To implement temperature measurement and control, the quenchant tester is equipped with a bridge circuit. The thermistor (which is one embodiment is in the form of a probe having a negative coefficient of resistance) is positioned in one leg of the bridge while the other three legs are fitted with resistors chosen to match the internal resistance of the thermistor at the desired operating temperature. Accordingly, when the power to the bridge is adjusted by way of a variable resistor positioned in series with the DC power supply energizing the bridge and a balanced condition is achieved, the thermistor will be at the prescribed operating temperature.

Relative thermal conductivity values for liquids may then be established in one of two ways; (1) the current flow to the circuit can be measured and the DC power in the thermistor calculated, or (2) the bridge can first be balanced with at least one reference fluid and bridge circuit voltage unbalance values observed when unknown fluids are subjected to the same power setting. For operating simplicity and cost considerations, the latter technique has been incorporated in the present invention. Although the bridge circuit voltage unbalance values noted are a function of the equilibrium temperature of the thermistor probe when immersed in the liquid, they are actually caused by and related to the thermal conductivity characteristics of the liquid. The greater the unbalance, the greater the difference in thermal conductivity between the reference and unknown liquid.

The portable quenchant tester of the present invention is a laboratory and field test device for accurately monitoring the quench-cooling performance of liquid quenchants in service. The tester is sensitive to small changes in quenchant condition and correlates well with the large scale laboratory cooling curve apparatus. In laboratory tests, the unit has been shown to offer a more reliable means for determining what is needed in restoring used quenchants than the viscosity and refractive index tests now used for field control. The tester is based upon a thermal conductivity measurement technique. A thermistor (thermal resistor) sensor electrically connected in one leg of a resistance bridge circuit is immersed in the test fluid sample. The bridge circuit, in cooperation with the thermistor sensor and a coupled power supply, act to provide a voltage deviation value across the bridge indicating the relative thermal conductivity or cooling capacity of the fluid. Incorporated electrical circuits, control and measurement devices ensure simple and reliable operation of the tester. The unit is reasonably inexpensive and compact. Fluid measurement requires only a few minutes times.

The apparatus and method of the present invention can be used for testing the thermal conductivity properties of any suitable liquid quenchant, including water, oils (i.e., hydrocarbons and high molecular weight organic compounds, both naturally-occurring and synthetic, which have similar properties), and aqueous solutions of various polymers. The method can be used with solutions of any water-soluble polymer suitable for use as a liquid quenchant, but the polymers are generally selected from polyalkylene glycols such as polyethylene glycol, polypropylene glycol, polybutylene glycol and the like; polyvinylpyrrolidone and substituted versions thereof, and polyacrylates, e.g., polymers of acrylic acid (substituted or unsubstituted) and esters thereof, and polyacrylamides. Mixtures of these polymers, and copolymers comprising at least two of the monomers used in their preparation, can also be used. If the quenchant to be tested is electrically conductive (such as, e.g., salt water), the thermistor and its electrical connections should be insulated to prevent short circuits.

Once the thermal properties of such a quenchant have been determined, the quenchant can be discarded and replaced, or purified, reconditioned or recycled. In a preferred embodiment of the present invention, a quenchant comprising an aqueous solution of a synthetic polymer is tested to determine the effective concentration of polymer (as reflected by thermal properties) and the polymer level adjusted to the desired level by adding a suitable quantity of the polymer, water or other diluent.

FIG. 1 illustrates schematically an embodiment comprising all of the elements necessary to the present invention. In particular, a thermistor 100 is a resistor element which is part of a bridge circuit shown in FIG. 1 as having resistors 3, 4 and 5.

The thermistor 100 used in this illustrative embodiment of the present invention is a Fenwel Electronic model GB32P62 glass bead type with a resistance of 27 ohms at 180° C. and approximately 10 ohms at 300° C. Although test temperatures ranging from 180° to 300° C. were investigated, a 180° C. temperature was found to be best suited for testing and accordingly the bridge circuit was fitted with 27 ohms resistors. However, it is contemplated as being withing the scope of the present invention to include any suitable resistance values for the circuits and not just the particular resistance values disclosed in the present embodiment.

If desired, temperature range changes can be easily made in the field by installing new resistors in the bridge circuit. Test sample size may be as little as one fluid ounce. Although the sample temperature need not be precisely controlled, all samples in a test series must be run at approximately the same temperature. Room or ambient temperature is most convenient.

In FIG. 1, the numeral 1 generally designates the apparatus of the present invention. The thermistor 100 is shown as being immersed in a liquid test sample 2. The thermistor 100 is included as one leg of the bridge circuit and is connected by wires 13 and 14 to the bridge circuit. A DC (direct current) power supply 11 supplies the bridge excitation volage and is connected along electrical lines 166 and 168 to the bridge circuit. A DC digital voltmeter 7 is connected by electrical lines 18 and 19 to the bridge circuit at terminals diagonally opposite those used to connect the power supply 11 to the bridge circuit. The digital voltmeter measures and displays the output voltage of the bridge circuit.

Block 6 in FIG. 1 represents a latch control, including a timer, for controlling the voltmeter display of the voltmeter 7 to latch the voltmeter display at the end of a predetermined period of time, e.g., 40 seconds after the beginning of a test, which beings with an initial 5 second warm-up, so that all tests will be conducted for the same predetermined period of time.

A voltage source 27 supplies AC current (usually at approximately 120 volts at 60 Hertz) to a timer and relay power on/off control circuit 12. Line 26 schematically indicates the supply of AC power to the DC power supply 11. Of course, in a detailed diagram, a return path for grounding would be shown for the power supply 11.

The controller 12 includes a timer to permit operation only during a predetermined amount of time, e.g., 45 seconds, to prevent overheating of the thermistor 100 as well as to control the length of the individual tests.

Another timer is includes in the DC voltage step control until 10. Here, for a short initial period of time, e.g., 5 seconds, a higher DC voltage is provided to the bridge circuit by applying the supply voltage through the fixed resistor 9 to rapidly raise the thermistor to approximately the operating temperature. The line 25 indicates generally and schematically the connection between elements 10 and 11 of FIG. 1. Also, line 22 schematically indicates the connection of the variable resistor 8 along line 24 to the DC voltage step control unit 10. The fixed resistor 9 is schematically shown connected by line 23 to line 24 which in turn connects to the unit 10.

Figure 2:
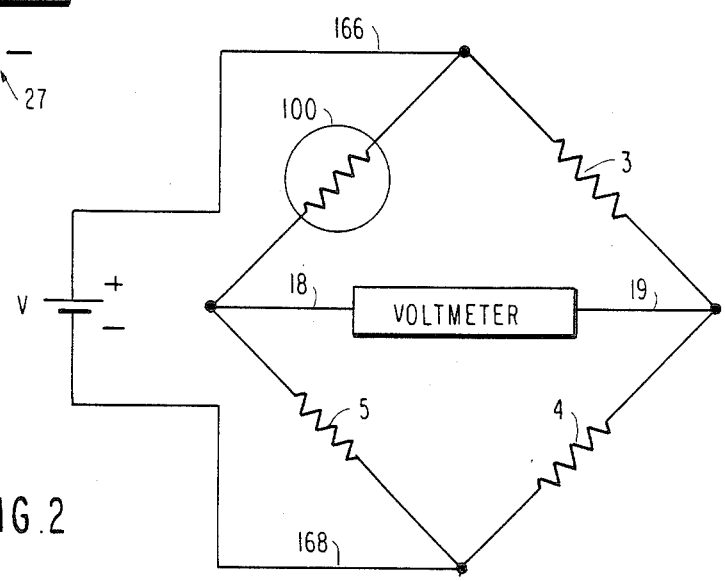
FIG. 2 is a schematic view of an alternative Wheatstone bridge circuit and the thermistor (schematically indicated) used in the bridge circuit.

FIG. 2 is a schematic diagram of an alternate Wheatstone bridge circuit for use in the circuit illustrated in FIG. 1, supplied by a direct current voltage source V. Line 166 and 168 connect the voltage source to the bridge circuit at diagonally opposed terminals, alternate to the position of the terminals used in the connection of the supply voltage to the bridge circuit of FIG. 1. A voltmeter is shown connected by lines 18 and 19 horizontally across the bridge circuit. While drawing virtually no power from the circuit, the voltmeter is capable of making very sensitive voltage measurements of the voltage across the bridge circuit indicated. The values of the resistances can be so chosen that 3 or 4 significant figures in the value of the resistance of thermistor 100 can be obtained. When the bridge is in balance, the usual bridge equation applies as follows: $R100/R5 = R3/R4$.

The positions of the battery and the voltmeter are interchangeable as indicated with respect to the connections shown in FIGS. 1 and 2. Furthermore, there are many modifications of the bridge shown which would adapt it to measurements of very low resistances, as well as to alternating current measurements (rather than the direct current measurements shown). Such are well-known in the prior art.

Although the basic test circuitry as described is rather simple in nature, additional elements are useful, and in the preferred embodiment it is preferred to incorporate a number of associated circuits for simple and reliable field operation. The unit thus preferably contains a DC power supply, three solid state timers, a push button operator switch, magnetic relay, two voltage adjustment potentiometers, a bridge balance potentiometer and a digital voltmeter positioned across the legs of the bridge. The complete system is contained in a cabinet measuring approximately $8'' \times 9'' \times 12''$.

Figure 3:
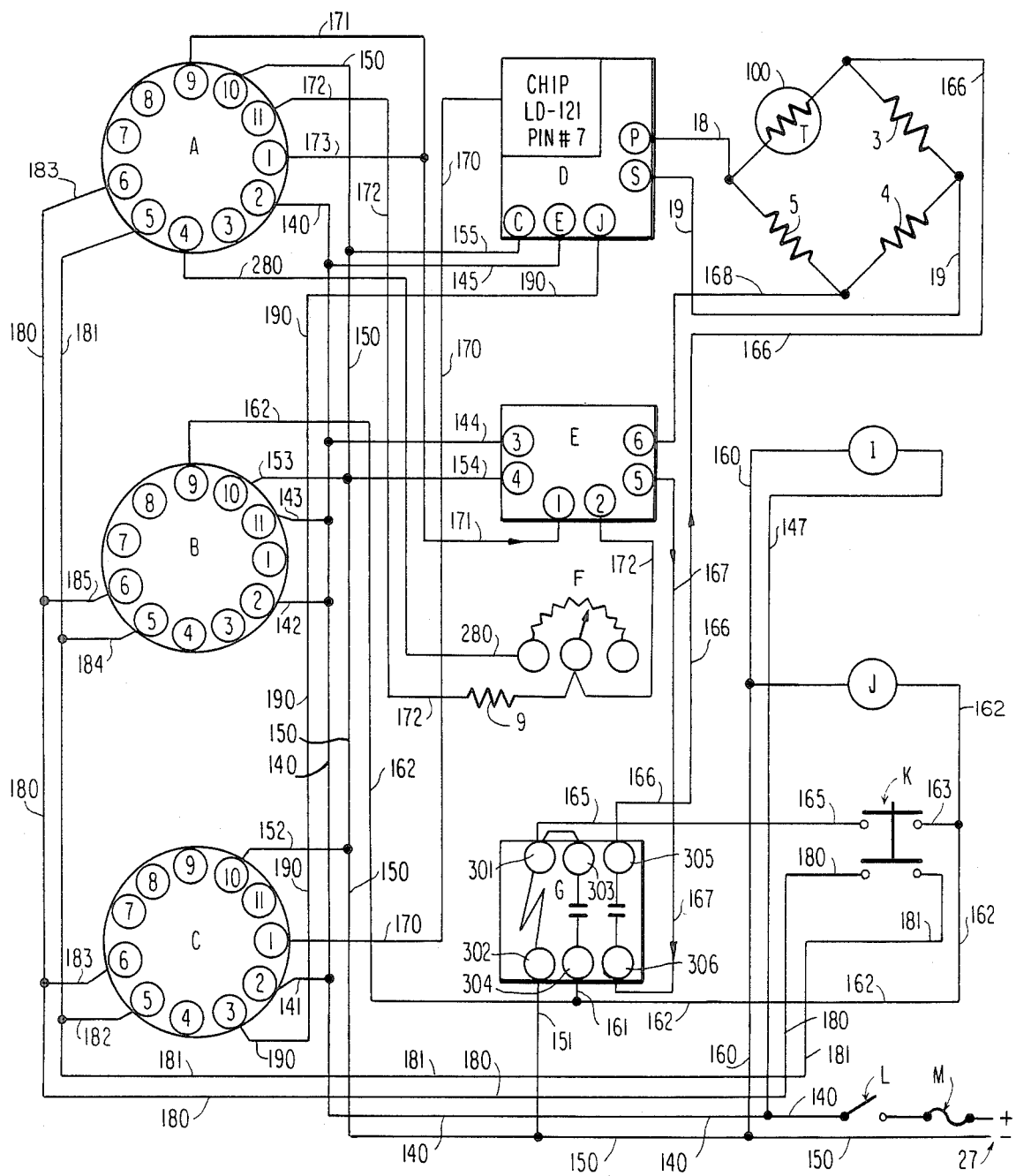
FIG. 3 is a more detailed electrical diagram of the circuit schematically illustrated in FIG. 1, indicating specific types of electrical apparatus and their interconnection to the Wheatstone bridge circuit illustrted in FIG. 2, which is substantially reproduced as a part of FIG. 3.

FIG. 3 is a more detailed schematic diagram of the apparatus used in the present invention. Several components are listed by capital letters A, B, C, D, E, F, G, H, I, J, K, L and M. Furthermore, FIG. 3 uses numerals within circles on each time delay relay A, B and C to designate contacts. The circled numbers 1–6 on electric power supply E designate terminals. Furthermore, circled letters C, E, J, P and S within voltmeter D designate terminals.

The reference number A designates a Dayton electronic time delay relay $6 \times 154A$ that is set for 5 seconds in the preferred embodiment. The device indicated by B is a Dayton electronic time delay relay $6 \times 154A$, which, in the preferred embodiment, is set for 45 seconds. The device indicated by C is a Dayton electronic time delay relay $6 \times 154A$, which, in the preferred embodiment, is set for 40 seconds.

The 45-second timer B permits a total powered operation time, e.g., of 45 seconds. For the first period of 5 seconds, timer A provides a higher than normal value of voltage and electrical power to the thermistor 100 to heat it to operating temperature. For the remaining 40 seconds, the bridge circuit is supplied with the normal operating voltage. At the end of the 45-second period, timer B terminates the DC power to the bridge circuit. Timer C provides a "latching" control signal to cause the reading of the voltmeter that is measured after 40 seconds to remain displayed after the power to the bridge circuit is terminated.

The voltmeter used is indicated as D, which is a Simpson digital voltmeter 2840. As indicated in FIG. 3, the voltmeter D includes a chip LD-121, PIN #7 which permits the activation of the display hold circuit so that latching of the voltage reading takes place.

The DC power supply E is a Sola electrical power supply 83-81-2250 and has six terminals. These terminals are represented by circles and are numbered consecutively, as terminals 1 to 6. The power supply E is equipped with an AC to DC converter, not shown, but conventional and well known in the art. The power supply is provided with AC power through terminals 3 and 4, and supplies DC power through terminals 1 and 2 for voltage control and subsequent application to the bridge circuit through terminals 5 and 6. Power supply E is a commerical unit, dscribed above, and its functions are well known and obvious to one of ordinary skill in the art.

A variable resistor F, designated in FIG. 1 as variable resistor 8, is shown in FIG. 3. More specifically, the variable resistor F is a potentiometer, which, in a preferred embodiment, is a 10-turn, 10K ohm potentiometer and is well known in the art. The potentiometer F and fixed resistor 9 are used in dual voltage control circuits with timer A for step control of the supply voltage to the bridge circuit. Resistor 9 is included within the circuit which is completed for the first 5-second interval of operation, thereby providing a relatively higher supply voltage to the bridge circuit for the purpose of heating thermistor 100. Potentionmeter F is included within the other circuit and is operator controlled for varying the supply voltage to the bridge circuit, at a lower voltage than is supplied through resistor 9.

In FIG. 3, relay G is a 2-pole, normally open (No), 120 volt 60 Hz coil relay having two opposed pairs of contacts. The normally open contacts are shown as having a gap between T-shaped elements connected to the circled terminals numbered 303–306 in FIG. 3. Terminals 301 and 302 are provided for energizing the 120 volt AC powered coil, indicated by the zig-zag lines connecting the terminals. Therminal 302 is connected to ground line 150 through line 151 and terminal 301 is connected to switch K through line 165. The normally open contacts which are located between terminals 303 and 304, as well as those between terminals 305 and 305, are closed upon energization of the relay coil. The closing of contacts 305 and 306 permits power to flow from DC power supply E to the Wheatstone bridge circuit by closing the circuit between terminals 5 and 6 of power supply E. Closing of contacts 303 and 304 causes continuous energization of the coil or latching of the relay during the 45-second interval of operation. Any suitable relay can be used as relay G.

The thermistor 100 used in this specific embodiment is a Fenwel Electronics thermistor GB32T62. However, any thermistor which is capable of being used, or modified to be used, in the present invention is contemplated as being within the scope of the present invention. The preferred choice of thermistor is a glass bead encased type with a negative temperature coefficient of resistance having an internal resistance of approximately 2000 ohms at 25° C. The preferred measurement or rest temperature of the thermistor is between 180° C. and 300° C. If a 180° C. test temperature is desired and the chosen thermistor is a 2000 ohm unit, such as Fenwel Electronics model GB32P62, the three resistors in the bridge circuit must have a resistance of approximately 27 ohms. However, the exact resistance value must be determined by an actual temperature-resistance calibration.

Elements represented by letters I and J respectively, are pilot lights of any suitable type. These are used to indicate that power is being supplied in the circuits in which the lights are connected.

Switch K is a pushbutton switch of the type designated as momentary contact, double pole single throw-normally open (MC, DPST-NO). Switch K is normally open and, upon pushing, simultaneously closes two pairs of contacts, one pair connecting line 163 with line 165 and the other connecting line 181 with line 180. Such switches are well known and conventional. In closing the first pair of contacts to connect lines 163 and 165, the relay G is energized. The lighting of the pilot light J indicates that the relay G has been energized. The second set of contacts closed by the switch K connects line 180 and 181 to close a circuit which is common to terminals 5 and 6 of each of the timers A, B and C. Thus, actuation of the switch K provides a simultaneous starting signal to synchronize the timing of each of the timers A, B and C. The AC power supply represented by numeral 27 supplies power through a fuse M which, in the present preferred embodiment, is a 2 amp fuse.

In the embodiment shown in FIG. 3, resistor 9 is a 400 ohm ¼ watt resistor. The fixed resistor 3, 4 and 5 of the bridge circuit are each, in the preferred embodiment, 27 ohm, 12 watt resistors. However, the present invention is not limited to these values, and any suitable resistors may be chosen for heightened selectivity and sensitivity for various expected thermistor operating ranges and conditions. The resistances may also be suitably selected for particular thermistor power capacities and resistances where various thermistors may be used instead of the thermistor identified in the preferred embodiment.

The connections and operation of the above-identified circuit elements are described hereunder. The functions of the various components of the tester of this invention and the electrical circuitry is best described through the sequence of test events which self-initiate in the equipment after depressing pushbutton K and those which are performed by the operator. After the operator has turned on the 120 volt AC power 27 to the test unit by closing switch L and has positioned the thermistor 100 in the test liquid, e.g., water, as required to initiate a test series on quenchants, the momentary contact test initiator switch pushbutton K is pressed and released. This action activates the 120 volt AC powered time delay relays, i.e., timers A, B and C, and initiates the timed off delay function of their contactors. It also energized the 120 volt AC powered coil of the power relay G causing its contactors (connected to terminals 305, 306) to close and direct DC power to the bridge circuit via lines 166, 167, 168 and thermistor 100. An electrical latch circuit to the power relay coil of relay G is completed through a second set of contactors (connected to terminals 303, 304) in the power relay and the contactors in the 45 second timer. This provides a continuance of AC power to the relay coil and therefore a continuance of of DC power to the bridge circuit for the timed interval, e.g., 45 seconds.

More specifically, when the AC power switch L is closed, power is supplied along lines 140, 150 to supply power to timer C at terminals 2 and 10 through lines 141 and 152 respectively; to timer B at terminals 2 and 10 through lines 142 and 153 respectively; to timer B at terminal 11 through lines 143; to the voltmeter D at terminals E and C (circled) through line 145 and 155 respectively; to the DC power supply E at terminals 3 and 4 (circled) through ines 144 and 154 respectively; to timer A at terminals 2 and 10; and to pilot light I through lines 147 and 160 respectively. The power supplied along lines 140, 150 and along each of the adjoining lines described above, is AC (alternating current) power. The ground line is illustrated as 150 which provides a ground to complete the circuit to allow power to flow through the various circuits as described hereunder.

When the switch K is closed, the contactors of timer B operate for 45 seconds to supply AC current to terminal 9 (circled). This allows current to flow through lines 162 and 163 across the momentarily depressed switch K to line 165 to thereby power the relay coil extending between terminals 301 and 302. As a result, the contacts between terminals 303 and 304, and terminals 305 and 306 are closed. The closing of the contacts between terminals 303 and 304 provides for current flow from line 162 along line 161 through terminals 304 and 303. The current then flows from terminals 303 and 301 across a short (unnumbered) jumper wire thereby supplying a continuance of AC power to the coil, and latching the relay in a closed state for the full 45 seconds.

In the latched condition, the relay G contacts connected to terminals 305 and 306 are closed so as to be in electrical communication with one another. This supplies DC current from the DC power supply E to the Wheatstone bridge circuit including resistors 3, 4 and 5 and thermistor 100. Thus, when the relay G is latched, DC power from terminal 5 of the DC power supply E flows through the contacts of terminals 306 and 305 along line 167 and to line 166, where power is supplied to the bridge circuitry described above. The circuit is completed by line 168 to the terminal 6 of the DC power supply E.

When the switch K is depressed, it also closed the contacts between lines 180 and 181, thereby providing the common simultaneous actuating signal to each of timers A, B and C. This is done since each of terminals 5 and 6 (circled) of each of the timers are connected respectively to wires 181 and 180. Timers A and C are connected through line 183 to wire 180 and timer B is connected to line 180 through line 185. Timers B and C are connected through lines 184 and 182 respectively to line 180, while time A is directly connected to line 181. Therefore, if power is permitted to flow through the conductors 180 and 181, each of the timers A, B and C are energized and powered and simultaneously being their timed functions.

Timer A is connected at terminals 1 and 9 (circled) to terminal 1 (circled) of power supply E through lines 171 and 173. Additionally, timer A is connected at terminal 11 (circled) to terminal 2 (circled) of power supply E through fixed resistor 9, by line 172. Also terminal 4 (circled) of timer A is connected to terminal 2 of power supply E through potentiometer F by line 280. These connections between timer A and power supply E provided for step control of the supply voltage to the bridge circuit and comprise the aforementioned dual voltage control circuits. During the first five seconds after initiation of timer A, the contactors provide a connection between terminals 9 and 11 (circled) of the timer A. This allows DC current to flow through resistor 9, which has a resistance substantially lower than potentiometer F, to thereby allow an increased voltage to be returned to voltage supply E for subsequent application of the supply voltage to the bridge circuit through terminals 5 and 6 (circled) of the power supply. At the termination of the 5-second interval, the contactors of timer A between terminals 9 and 11 (circled) are opened. For the remaining 40 seconds, the contactors between terminals 1 and 4, which are closed for the full 45-second period, provide a return supply of DC power through potentiometer F to power supply E. Adjustment of the potentiometer, then, allows the operator to control the voltage supplied to the bridge circuit through terminals 5 and 6 of the power supply. Therefore, the first 5 seconds of timer A provide for a higher than normal supply voltage to the bridge circuit for the purpose of heating thermistor 100. Thereafter, the supply voltage can be adjusted to balance the bridge circuit, as desired.

Voltmeter D is connected across two points (unnumbered) of the Wheatstone bridge circuit. Line 18 connects the positive terminal P of voltmeter D with one of the points of connection, and line 19 connects negative terminal S to the other point of connection. Therefore, voltage measurements of the voltage across the bridge circuit can be made using voltmeter D.

In conducting a test with this aparatus to determine the quench-cooling properties of a quenchant, a series of tests are performed to establish reference measurements based on the known quench-cooling properties of fresh quenchants. The first test, which establishes a baseline for the results of the subsequent tests, can be conducted on water. At least one additional test is then run on a fresh quenchant having a known quench-cooling property. Thereafter, a single test run on an unknown quench-cooling property quenchant will yield a determination of that quenchant's relative quench-cooling property.

The first test is conducted by immersing thermistor 100 in a quenchant, such as $H_2O$, to establish a baseline for the subsequent tests. Switch L is closed to supply AC power to the apparatus. When it is desired to begin the test, switch K is momentarily depressed thereby activating the initiation of timers A to C and closing the contacts of coil F. The sequence of the test begins with timer A supplying a high excitation voltage to the bridge circuit. At the conclusion of the high voltage interval, the operator adjusts the panel mounted voltage control potentiometer F for a bridge balance condition. as indicated by the display on the digital voltmeter D, and continues to do so until the contactors of the 40 second timer C activate the display hold circuit of the voltmeter D. This is done by interrupting the connection made through timer C between terminal J which is connected through line 190 to timer C and pin No. 7 of chip LD-121 which is connected through line 170 to the timer at terminals 1 and 3 (circled) respectively. At this point the test run is completed and the bridge circuit voltage display is locked on the screen of the voltmeter D, 40 seconds after pressing pushbutton K. Subsequently, timer B interrupts the latch circuit of relay G to the power relay coil and the DC power to the bridge circuit is terminated 45 seconds after pressing pushbutton K.

The automatic test termination and power off feature insure that all tests in a series terminate at the same time after the initially rapid change in thermistor temperature and resistance has moderated and a near equilibrium condition has been achieved. It also protects against thermistor burn out due to the inadvertent continuance of power to the thermistor after the run is completed and the thermistor has been removed from the liquid.

As a result of conducting this first baseline test, a bridge circuit balance condition has been established with water and the bridge circuit supply voltage has been fixed by locking the setting on the operator controlled voltage adjustment potentiometer F. Comparative testing of fresh and used quenchants of the same type may now being. At least one test needs to be conducted on a fresh quenchant having a known quench-cooling property. To implement this test phase the thermistor probe 100 is immersed in the fresh fluid and the test initiate button K is depressed. Timer A supplies the high level of excitation voltage to the bridge circuit. However, at the conclusion of the high voltage period the operator does not adjust the level of excitation voltage to achieve a bridge balance condition. Instead, the bridge unbalance is measured and the final voltage deviation appears on the display screen of the voltmeter D.

Bridge circuit unbalance occurs with the new and used quenchants because these materials have a lower thermal conductivity or cooling rate than water and accordingly the thermistor becomes hotter and lower in electrical resistance as the current flows. The greter the unbalance noted the lower the cooling rate of the product. Because the variation in resistance of the thermistor with changing temperature, and the bridge circuit voltage unbalance with changing resistance in one leg are both nearly logarithmic functions, but acting in opposite directions, the voltage unbalance values observed with the quenchant tester may be considered a nearly linear function of the thernal conductivity of the fluid. In addition, these values may be used to establish the polymer content of fresh liquid quenchants and the apparent or effective polymer content of used quenchants. For example, the bridge is set for zero voltage deflection or a balance condition with water alone. If subsequently a bridge deflection of Y volts is noted with a fresh 40 precent polymer solution and a value of $\frac{1}{2}$ Y is observed with a used material, the used material is calculated to have an effective cooling rate equal to a fresh 20 percent solution. Where many samples of similar quenchants are to be tested, the voltage imbalance readings can be converted directly to the polymer concentrations by means of a graph, conversion table or nomogram; or the voltmeter can be an analog instrument fitted to read directly in terms of polymer concentration. With this information available the used quenchant solution may be corrected to a desired cooling rate by the addition of a measured amount of fresh quenchant or water as required.

To test a liquid quenchant sample 2 or a series of used samples of the same type quenchant, the operator simply establishes a control or reference value for a fresh solution of similar material having a known concentration of polymer. The voltage value derived with the used material(s) is then compared to the fresh material voltage value to determine the effective polymer (quenchant) concentration. This may be done by a simple proportion equation or if desired from a curve or nomogram established by running two or more fresh samples having range of quenchant concentration.

Although specific devices have been shown having specific electrical circuit configurations, this is merely a preferred embodiment of the present invention, and the present invention is not limited thereto. Each of the items of apparatus specifically identified in the preferred embodiment has many equivalents in the prior art, and such equivalents would clearly be matters of choice, as would other control arrangements having the same end result as in the present preferred embodiment. Furthermore, although specific test time interval periods have been set, namely 5 seconds, 40 seconds, and 45 seconds, predetermined time intervals may be used which are suitable for the particular fluid being tested and for the particular thermistor used, as well as the other circuit apparatus used for control purposes. An operator could manually adjust the DC voltage at the appropriate, exact time intervals and perform all of the tests, performed by the tester of this invention. However, this would be somewhat cumbersome and very difficult to do consistently and therefore the apparatus of this invention, results in a convenient, portable test unit which preferably has the elements enclosed within a cabinet which can be carried by the test operator.

In the tester and testing method of this invention, the thermistor 100 provides a very sensitive indication of thermal conductivity of the liquid in which it is immersed. Since it has a negative coefficient of resistance (that is, the hotter the thermistor becomes, the lower its resistance), the thermistor provides the double function of introducing the heat into the test sample and providing an electrical indication of the equilibrium temperature achieved by the thermistor during its operation.

Quenchant test sample size may be as little as one fluid ounce. Although the sample temperature need not be controlled at a given point, all samples in a test series must be run at the same temperature. Room temperature is most convenient. Sample agitation is not required or desired during testing.

Although the basic test circuitry of the quenchant tester of this invention is uncomplex in design, other features have been incorporated to insure repeatable high quality test results and uncomplicated operation for laboratory and field usage. The circuitry is housed in a suitably small cabinet measuring $8 \times 9 \times 12$ inches with operator control and readout equipment mounted on the front panel. Contained in the cabinet is a 120 volt AC powered variable 9 to 12 volt DC power supply, an electric power relay, the bridge circuit resistor, and three adjustable solid state timed off delay relays; one set for 5 seconds, the second for 40 seconds and the third for 45 seconds.

The effectiveness, reliability and sensitivity of the apparatus and method of the present invention will be seen from the following non-limiting examples. Tests show that the novel tester accurately measures the quenchant concentration present in fresh solutions with an accuracy of ±0.5%.

EXAMPLE 1

Using a quenchant tester of the present invention as described above, quenchant solutions of various concentrations were tested, and it is determined that the concentrations of polymer in these aqueous solutions could be measured to a precision of approximately ±0.5 weight percent. Trials were then performed on samples of used quenchant solutions to determine whether the tester could provide a sufficiently sensitive indication of the quench-cooling performance of such material and provide the bases for the correction of used quenchant baths to restore their properties to the desired standard when necessary.

The tester was calibrated as described above with distilled (or tap) water and, as a second test standard, an aqueous solution of fresh unused UCON ® Quenchant HT, i.e., UQHT, (an aqueous solution of a mixed polyalkylene glycol prepared by copolymerizing ethylene and propylene oxides and having a weight average Mw of about 15,000). The UQHT test solution contained about 40 weight percent polymer. The tester was then used to test a sample of used UQHT from an automative spring manufacturing plant. The quenchant solution was originally about 40 weight percent polymer, but the used sample was found to have a cooling rate equivalent to a solution containing 53 weight percent polymer.

Comparative tests using standard refractometer apparatus indicated that the used sample had a cooling rate equivalent to a polymer concentration of 45 weight percent.

Comparative tests using standard kinematic viscosity apparatus indicated that the used sample had a cooling rate equivalent to a polymer concentration of 42 weight percent.

To determine the accuracy of the cooling rate information determined by the novel quenchant tester, compared to that developed from standard refractometer and viscosity tests, a fresh unused quenchant solution containing 53 weight percent polymer was prepared to match the percent polymer indicated by the tester and a solution containing 42 weight percent polymer was prepared to match the percent polymer suggested by viscosity measurement.

Figure 4:
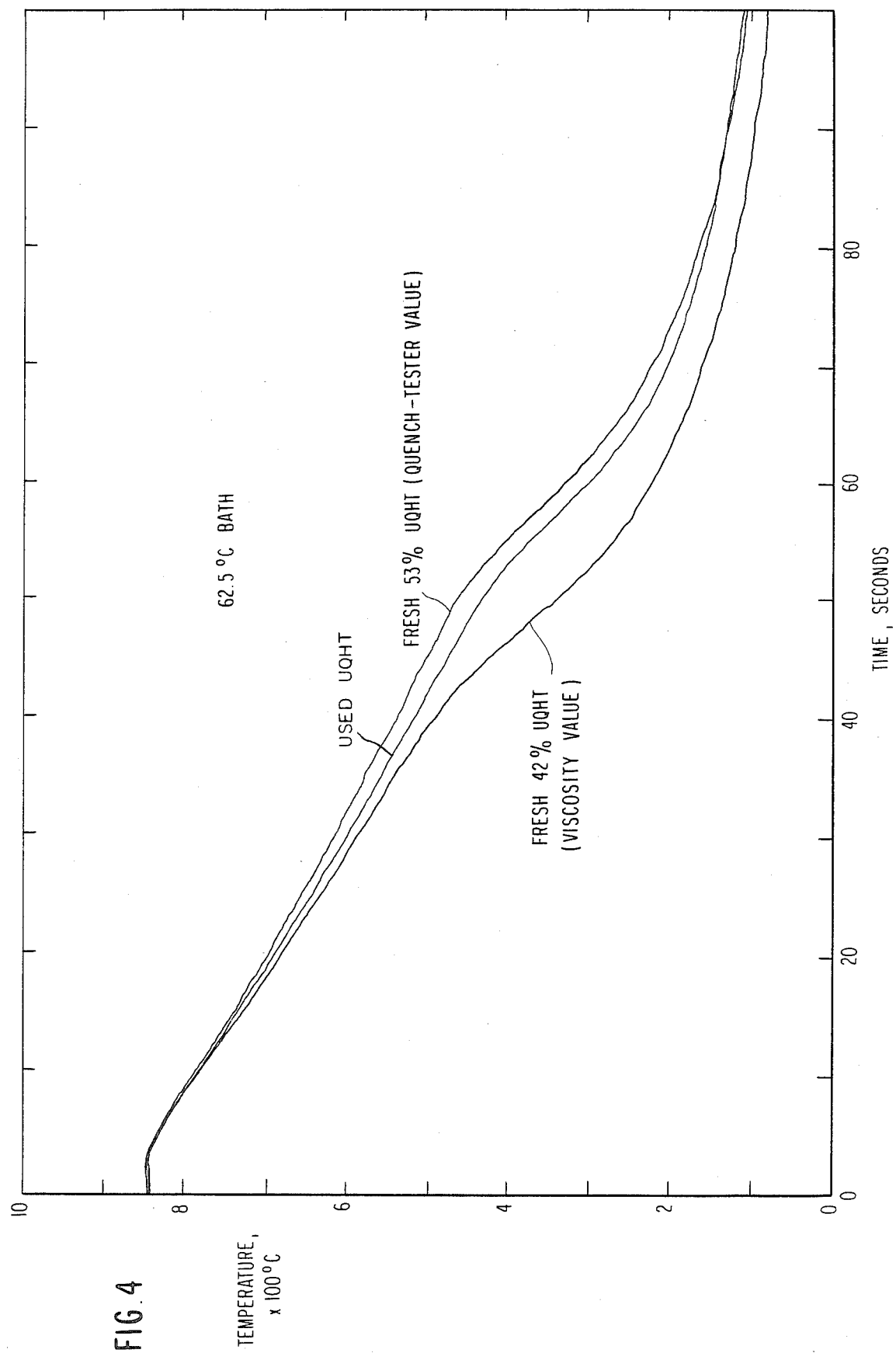
FIG. 4 illustrates quenchant cooling curves determined by various methods to illustrate the utility of the present invention.

Using standard laboratory test procedures and apparatus for cooling curve analysis, the cooling rates of the used UQHT quenchant sample and the two fresh unused solutions (53 wt. % and 42 wt. %) were compared. In the cooling curve analysis, a truncated cone of metal, approximately one inch in diameter and 1.5 inches long, having a thermocouple in the center and another on the surface, is heated, immersed in the liquid to be tested, and allowed to cool, while a plot of temperature versus time is developed using normal recording equipment. The resulting curves for two different bath tempertures are shown in FIGS. 4 and 5. Using a bath temperature of 62.5° C., FIG. 4 shows that the cooling curve for the used UQHT quenchant sample lies just below the curve for the 53 percent solution, and is considerably above the curve for the 42 percent solution for most of its length. Using a bath temperature of 75° C., FIG. 5 shows that the cooling curve for the used sample lies slightly above that for the 53 percent sample, and is farther removed from the curve for the 42 percent solution over most of the length. In both instances, the cooling curve of the fresh unused 53% UQHT solution (suggested by the novel quench tester) more closely approximates the cooling curve of the unused UQHT than does the cooling curve of the fresh 42% UQHT solution which was suggested by the viscosity techniques. It is therefore apparent that in addition to providing faster and more convenient testing of such samples than either refractometer or viscosity testing, the tester of the present invention provides a more accurate evaluation of the cooling rate of the used quenchant sample than the viscosity testing method. The quenchant tester of this invention more accurately predicted the quenchant concentration and cooling curve characteristics of this used UQHT quenchant than either the refractive index or viscosity methods of the prior art.

EXAMPLE 2

Using the same novel quenchant tester and procedures as in Example 1, the tester was calibrated with water and an unused aqueous solution of UQHT as described in Example 1, the fresh unused test solution having a polymer concentration of 20 weight percent.

The tester was then used to test a sample of used UQHT from a forging plant. The used UQHT solution was originally about 20 wt. % polymer, but the used sample was found to have a cooling rate equivalent to a fresh unused UQHT solution containing about 22 wt. % polymer. Using refractometer and viscosity measurements as described in Example 1, the used sample was determined to have a quenchant concentration equivalent to 26 and 25 wt. % of fresh unused UQHT, respectively. Cooling curves prepared using the method described in Example 1 for the used UQHT sample showed its properties to be nearly equivalent to a polymer concentration of 20 wt. %. Thus, the quenchant tester of the present invention more accurately predicted the properties of the sample (as described by the cooling curves, i.e., as 22 wt. % polymer) than did either the refractive index (26 wt. %) or viscosity (25 wt. %) techniques.

EXAMPLE 3

A used sample of UCON ® Quenchant B, hereinafter called UQB, which had been used in a laboratory repeat quench (R/Q) test (a lab test method designed to stress the durability of the quenchant), i.e., the repeat quench test was conducted using the novel tester and procedures of Example 1 and the quenchant was determined to have a quenchant concentration equivalent to about 10.5 wt. % polymer. Quenchant UQB is an aqueous solution of a mixed polyalkylene glycol as with Quenchant HT, but having a weight average molecular weight (MW) of approximately 22,000. While monitoring with the novel quenchant tester, a fresh, unused, UQB quenchant polymer was added until the amount of bridge circuit unbalance was equal to that produced by a fresh, unused, UQB quenchant solution containing exactly 20 wt. % polymer.

Using the apparatus and procedures described in Example 1, cooling curves were developed for (1) the used UQB quenchant sample, (2) the used UQB quenchant sample as adjusted to the equivalent of 20 wt. % polymer, and (3) a fresh, unused, UQB quenchant solution containing 20 wt. % polymer, using two bath temperatures, 25° C. and 50° C., respectively. These curves, shown in FIGS. 6 and 7, indicate that the used UQB sample adjusted to the equivalent of 20 wt. % polymer and the fresh UQB 20 wt. % polymer solution provide essentially the same cooling rates, thus demonstrating that the quenchant tester and procedures of the present invention can be successfully used to adjust the quenchant concentration and coolilng characteristics of used quenchant solutions.

The present invention is capable of achieving all of the above-enumerated objects, and while a preferred embodiment has been set forth, the scope of the present invention is not limited thereto but may be embodied within the scope of the following claims.

What is claimed is:

1. An apparatus for testing the quench-cooling properties of a liquid quenchant, comprising:
   a thermistor adapted to be immersed in the liquid to be tested;
   means for applying an electric potential across said thermistor comprising means for supplying an excitation voltage to a Wheatstone bridge circuit which contains said thermistor in one leg thereof;
   first timing means for controlling a first interval of time during which said electric potential is applied across said thermistor;
   means for determining the relative electrical resistance of said thermistor, including means for measuring voltage across two points of said Wheatstone bridge circuit, said voltage measuring means having means for latching and indicating measured voltage;

said first timing means having a first timer for controlling a first interval of time during which said excitation voltage is supplied to said Wheatstone bridge;

a second timer for controlling a second interval of time during which a first predetermined level of voltage is provided to said Wheatstone bridge circuit; and a third timer for controlling a third interval of time and for actuating said latching means after the expiration of said third interval of time to provide an indication of voltage of said means for measuring voltage whereby the relative electrical resistance is determined from measuring voltage across said two points of said bridge circuit as said indication of voltage after said third interval of time, and further whereby said indication of voltage is compared with a reference indication of voltage obtained by testing a reference liquid quenchant with said apparatus for determining comparative quench-cooling properties of said liquid quenchant in comparison with said reference liquid quenchant.

2. An apparatus as claimed in claim 1, wherein said thermistor has a negative temperature coefficient of resistance.

3. An apparatus for testing the quench-cooling properties of a liquid quenchant, comprising:

a thermistor adapted to be immersed in the liquid to be tested;

means for applying an electric potential across said thermistor, comprising means for supplying an excitation voltage to a Wheatstone bridge circuit that contains said thermistor in one leg thereof;

means for maintaining said excitation voltage at a first predetermined level for a first predetermined period of time;

means for maintaining a second predetermined level of excitation voltage for a second predetermined period of time;

means for measuring an output voltage across said Wheatstone bridge; and means for holding a reading of said output voltage after a third predetermined period of time, whereby the reading of said output voltage of said holding means is compared with a reference voltage value obtained by testing a reference liquid quenchant with said apparatus for determining comparative quench-cooling properties of said liquid quenchant in comparison with said reference liquid quenchant.

4. An apparatus according to claim 3, wherein said means for maintaining a second predetermined level of excitation voltage comprises an adjustable voltage supply means such that a balance of said bridge circuit can be obtained by adjusting said adjustable voltage supply means.

5. An apparatus as claimed in claim 4, wherein said means for maintaining said excitation voltage at a first predetermined level comprises a fixed voltage supply means for supplying excitation voltage at a level higher than the voltage supplied to said bridge circuit by said adjustable voltage supply means for heating said thermistor for said first predetermined period of time.

6. A process for determining an amount of polymer quenchant additive or water required to be added to a quenchant comprising an aqueous solution of a polymer to alter the quenchant properties of said quenchant to a desired value, comprising the steps of:

testing a sample of said quenchant using a thermistor;

providing three resistors, each having a predetermined resistance, with said thermistor in a bridge circuit;

immersing said thermistor in said sample and applying an electric potential across said thermistor by supplying an excitation voltage to said bridge circuit for a predetermined period of time;

determining a relative electrical resistance of said thermistor by measuring an output voltage across said bridge circuit after said predetermined period of time using means for measuring voltage to obtain a measured voltage value;

comparing the measured voltage to at least one reference measured voltage value obtained by testing a reference liquid quenchant according to said process to obtain a difference in concentration of polymer quenchant additive between said quenchant and said reference liquid quenchant; and using said difference to determine an amount of polymer quenchant additives or water necessary to be added to said quenchant in order to alter the quench-cooling properties of said quenchant to said desired value.

7. A process in claim 6, further comprising in the step of using said thermistor, the step of preheating said thermistor to initially lower its resistance at the beginning of a test sequence;

subsequently reducing the voltage supplied to said thermistor to a predetermined level for said predetermined period of time; and whereby each test conducted using said thermistor is conducted for an equal predetermined period of time.

8. A process determining an amount of polymer quenchant additive or water required to be added to a quenchant comprising an aqueous solution of a polymer to alter the quenchant properties of said quenchant to a desired value, comprising the steps of:

testing a sample of said quenchant using a thermistor;

providing three resistors, each having a predetermined resistance, with said thermistor in a bridge circuit;

immersing said thermistor in said sample and applying an electric potential across said thermistor by supplying an excitation voltage to said bridge circuit;

determining a relative electrical resistance of said thermistor by measuring an output voltage across said bridge circuit using means for measuring voltage to obtain a measured voltage value;

providing a first reference measured voltage value obtained by testing a first reference liquid quenchant using said thermistor immersed in said first reference quenchant liquid according to said process;

taking a second reference measured voltage value of a second reference liquid quenchant by testing said second reference liquid quenchant using said thermistor according to said process;

comparing the difference between the second measured value and the first measured value with the difference between said quenchant sample measured value and said first reference measured value; and determining a ratio of said differences and using said ratio as a proportionate indicator of the amount of quenchant additive or water to be added to said quenchant in order to obtain said desired value.

9. A process for determining an amount of polymer quenchant additive or water required to be added to a quenchant comprising an aqueous solution of a polymer to alter the quenchant properties of said quenchant to a desired value, comprising the steps of:

testing a sample of said quenchant using a thermistor;

providing three resistors, each having a predetermined resistance, with said thermistor in a bridge circuit;

immersing said thermistor in said sample and applying an electric potential across said thermistor by supplying an excitation voltage to said bridge circuit;

determining a relative electrical resistance of said thermistor by measuring an output voltage across said bridge circuit using means for measuring voltage to obtain a measured voltage value;

providing a first reference measured voltage value obtained by testing first reference liquid quenchant using said thermistor immersed in said first reference quenchant liquid according to said process;

using a first timing sequence for controlling the supplying of said excitation voltage at a predetermined level of power to said bridge circuit for heating said thermistor for an interval of time;

using a second timing sequence for controlling the supplying of said excitation voltage at a second adjustable level of electrical power for a predetermined period of time;

using a third timing sequence for latching said means for measuring voltage to hold said measured voltage;

comparing said measured voltage to at least one reference measured voltage value obtained by testing a reference liquid quenchant according to said process to obtain a difference in concentration of polymer quenchant additive between said quenchant and said reference liquid quenchant; and using said difference to determine an amount of polymer quenchant additives or water necessary to be added to said quenchant in order to alter the quenchant properties of said quenchant to said desired value.

10. A method for determining the relative quench-cooling property of a quenchant comprising the steps:

using a thermistor connected in a Wheatstone bridge circuit immersed in a quenchant to be tested;

immersing said thermistor in a first quenchant having a known quench-cooling property, supplying a predetermined level of excitation voltage to said Wheatstone bridge circuit for preheating said thermistor for a first period of time, and thereafter adjusting the level of said excitation voltage to a second level wherein said Wheatstone bridge is substantially balanced after a second period of time;

immersing said thermistor in a second quenchant having a known quench-cooling property, supplying said first predetermined level of excitation to said Wheatstone bridge circuit for preheating said thermistor for said first period of time and thereafter supplying said excitation voltage at said second level so that said Wheatstone bridge is unbalanced at a first level of bridge unbalance after second period of time in an amount directly proportional to the change in the quench-cooling property of said second quenchant from said first quenchant;

immersing said thermistor in a third quenchant having an unknown quench-cooling property, supplying said first predetermined level of excitation voltage to said Wheatstone bridge circuit for preheating said thermistor for said first period of time and thereafter supplying said excitation voltage at said second level to said Wheatstone bridge circuit so that said Wheatstone bridge is unbalanced at a second level of bridge unbalance after said second period of time in an amount directly proportional to the change in the quench-cooling property of said third quenchant from said first quenchant; and determining the relative quench-cooling property of the third quenchant by comparing said first level of bridge unbalance with said second level of bridge unbalance.

11. An apparatus for testing the quench-cooling properties of a liquid quenchant, comprising:

a thermistor adapted to be immersed in the liquid to be tested;

means for applying an electric potential across said thermistor including means for supplying an excitation voltage to a Wheatstone bridge circuit which contains said thermistor in one leg thereof;

first timing means for controlling a first interval of time during which said electric potential is applied across said thermistor;

means for determining the relative electrical resistance of said thermistor, including means for measuring voltage across two points of said Wheatstone bridge circuit, said voltage measuring means having means for latching and indicating the measured voltage; and whereby the relative electrical resistance is determined from measuring voltage across said two points of said bridge circuit as an indication of voltage held by said latching means before the expiration of said first interval of time, and further whereby said indication of voltage is compared with a reference indication of voltage obtained by testing a reference liquid quenchant with said apparatus for determining comparative quench-cooling properties of said liquid quenchant in comparison with said reference liquid quenchant.

12. An apparatus as claimed in claim 11, wherein said means for applying an electrical potential across said thermistor further comprises:

adjustable voltage supply means for supplying said excitation voltage to said bridge circuit such that a bridge balance can be obtained by adjusting said adjustable voltage supply means.

13. An apparatus as claimed in claim 11, wherein said means for applying further comprises means for applying a first predetermined level of voltage higher than said excitation voltage to said thermistor through said Wheatstone bridge to preheat said thermistor.

14. An apparatus as claimed in claim 13, further comprising second timing means for controlling an interval of time during which said first predetermined level of voltage is applied.

15. An apparatus as claimed in claim 14, further comprising third timing means for controlling an interval of time after which said latching means are actuated to provide said indication of voltage at said means for measuring voltage.

16. An apparatus as claimed in claim 12, wherein said means for applying an electric potential across said thermistor further includes fixed voltage supply means for supplying said excitation voltage to said bridge circuit at a higher voltage than the voltage that is supplied to said bridge circuit by said adjustable voltage supply means for preheating said thermistor for a predetermined period of time shorter than said first interval of time.

* * * * *